(12) United States Patent
Soper et al.

(10) Patent No.: US 9,174,902 B2
(45) Date of Patent: Nov. 3, 2015

(54) REMOVAL OF ORGANIC SALTS FROM BIO-DERIVED GLYCOL PRODUCTS OF POLYOL HYDROGENOLYSIS

(71) Applicant: ARCHER DANIELS MIDLAND COMPANY, Decatur, IL (US)

(72) Inventors: John G. Soper, Mt. Zion, IL (US); William Christopher Hoffman, Decatur, IL (US); Chi-Cheng Ma, Forsyth, IL (US)

(73) Assignee: Archer Daniels Midland Co., Decatur, IL (US)

( * ) Notice: Subject to any disclaimer, the term of this patent is extended or adjusted under 35 U.S.C. 154(b) by 0 days.

(21) Appl. No.: 14/419,549

(22) PCT Filed: Aug. 21, 2013

(86) PCT No.: PCT/US2013/055903
§ 371 (c)(1),
(2) Date: Feb. 4, 2015

(87) PCT Pub. No.: WO2014/035740
PCT Pub. Date: Mar. 6, 2014

(65) Prior Publication Data
US 2015/0218069 A1    Aug. 6, 2015

Related U.S. Application Data

(60) Provisional application No. 61/694,288, filed on Aug. 29, 2012.

(51) Int. Cl.
*C07C 29/76* (2006.01)
*C07C 29/132* (2006.01)
*C07C 29/84* (2006.01)
*C07C 29/80* (2006.01)
*C07C 29/74* (2006.01)

(52) U.S. Cl.
CPC ............... *C07C 29/76* (2013.01); *C07C 29/132* (2013.01); *C07C 29/74* (2013.01); *C07C 29/80* (2013.01); *C07C 29/84* (2013.01)

(58) Field of Classification Search
None
See application file for complete search history.

(56) References Cited

U.S. PATENT DOCUMENTS

| 2008/0274019 | A1* | 11/2008 | Beggin et al. ................. 422/129 |
| 2009/0030243 | A1* | 1/2009 | Soest et al. .................... 568/870 |
| 2012/0088941 | A1* | 4/2012 | Soest et al. .................... 568/870 |

* cited by examiner

*Primary Examiner* — Brian J Davis
(74) *Attorney, Agent, or Firm* — Vincent T. Kung

(57) ABSTRACT

A method for reducing contaminants in the production of a bio-derived glycol product of polyol hydrogenolysis is described. The method involves subjecting an aqueous, polyol product mixture (from the hydrogenolysis conversion of biologically-derived carbohydrate feedstock) to ion-exclusion chromatography to separate and reduce impurities from an eluant fraction containing a desired product, and distilling the eluant fraction to yield the desired product (e.g., propylene glycol or ethylene glycol). The reaction product mixture can be introduced into a continuous ion-exclusion chromatography system to reduce the impurities and produce in a high-throughput manner a finished otherwise commercially acceptable glycol product.

20 Claims, 5 Drawing Sheets

REMOVAL OF ORGANIC SALTS FROM BIO-DERIVED GLYCOL PRODUCTS OF POLYOL HYDROGENOLYSIS

BENEFIT OF PRIORITY

The present application claims benefit of priority of U.S. Provisional Application No. 61/694,288, filed on Aug. 29, 2012, the contents of which are incorporated herein.

FIELD OF INVENTION

The present invention relates generally to processes for producing propylene glycol or ethylene glycol by the hydrogenolysis of polyols. In particular, the invention pertains to & process for refining the hydrogenolysis product to provide propylene glycol and ethylene glycol in a commercially attractive yield and purity.

BACKGROUND

Traditionally, propylene glycol (PG and ethylene glycol (EG) have been produced from petrochemical sources. The current industrial or commercial route to produce propylene glycol is by the hydration of propylene oxide converted from petroleum-derived propylene by either the chlorohydrin process or the hydroperoxide process (A. E., Martin, F. H. Murphy, 4th ed. Kirk-Othmer Encyclopedia of Chemical Technology, vol. 17, Wiley, New York, 1994. p. 715; D. T. Trent, 4th ed. Kirk-Othmer Encyclopedia of Chemical Technology, vol. 20, Wiley, New York, 1996, p. 271). The commercial production of ethylene glycol involves the hydration of ethylene oxide, made by the oxidation of ethylene. Propylene and ethylene are industrial by-products of gasoline manufacture, for example as by-products of fluid cracking of gas oils or steam cracking of hydrocarbons.

The world's supply of petroleum is being depleted at an Increasing rate. Eventually, demand for petrochemical derived products will outstrip the supply of available petroleum. When this occurs, the market price of petroleum and, consequently, petroleum derived products will likely increase, making products derived from petroleum more expensive and less desirable. As the available supply of petroleum decreases, alternative sources and, in particular, renewable sources of comparable products will necessarily have to be developed. One potential renewable source of feedstocks for producing such comparable products is bio-based matter, such as agricultural and forestry products. Use of bio-based products may potentially counteract, at least in part, the problems associated with depletion of the petroleum supply.

Catalytic hydrogenolysis (hydrocracking) conversion of carbohydrate-based feedstocks, such as five and six carbon-unit polysaccharides and/or sugar alcohols (conventionally, glycerol, glycols, or sorbitol), involves reacting the carbohydrate-based feedstocks with hydrogen to produce compounds that are referred to as "polyols" or "polyhydric alcohols." The reaction with hydrogen breaks down the carbohydrate molecules into fragments of lower molecular weight.

For instance, U.S. Pat. No. 5,206,927 describes a homogeneous process for hydrocracking carbohydrates in the presence of a soluble, transition metal catalyst to produce lower polyhydric alcohols. A carbohydrate is contacted with hydrogen in the presence of a soluble transition metal catalyst and a strong base at a temperature of from about 25° C. to about 200° C. and a pressure of from about 15 to about 3000 psi. Other processes, for example, in U.S. Pat. Nos. 5,276,181 and 5,214,219, involve hydrogenolysis of glycerol using a copper and zinc catalyst in addition to a sulfided ruthenium catalyst at a pressure over 2100 psi and temperature between 240-270° C. U.S. Pat. No. 5,616,817 describes a process of preparing 1,2 propanediol (propylene glycol) by catalytic hydrogenolysis of glycerol at elevated temperature and pressure using a catalyst comprising the metals cobalt, copper, manganese and molybdenum. German patent DE 541362 describes the hydrogenolysis of glycerol with a Nickel catalyst, while U.S. Pat. No. 4,476,331 describes a two stage method of hydrocracking carbohydrates (for example glucose), wherein a modified ruthenium catalyst is used for hydrocracking sorbitol to produce glycerol derivatives. European Patent applications EP-A-0523 014 and EP-A-0 415 202 describe a process for preparing lower polyhydric alcohols by catalytic hydrocracking of aqueous sucrose solutions at elevated temperature and pressure using a catalyst whose active material comprises the metals cobalt, copper and manganese. Persoa & Tundo (Ind. Eng. Chem. Res. 2005, 8535-8537) describe a process for converting glycerol to 1,2-propanediol by heating under low hydrogen pressure in presence of Raney nickel and a liquid phosphonium salt. Selectivities toward 1,2-Propanediol as high as 93% were reported, but required using a pure glycerol and long reaction times (20 hrs.), Crabtree et al. (Hydrocarbon processing, February 2006, pp. 87-92) describe a phosphine/precious metal salt catalyst that permit a homogenous catalyst system for converting glycerol into 1,2-PD. However, low selectivity (20-30%) was reported. Other reports indicate use of Raney Copper (Montassier et al. Bull. Soc. Chim. Fr. 2 1989 148; Stud. Surf. Sci. Catal. 41 1988 165), copper on carbon (Montassier et al. J. Appl. Catal. A 121 1995 231)), copper-platinum and copper ruthenium (Montassier et al. J. Mol. Catal. 70 1991 65). Other homogenous catalyst systems such as tungsten and Group VIII metal-containing catalyst compositions have been also tried (U.S. Pat. No. 4,642,394). Miyazawa et al. (J. Catal. 240 2006 213-221) & Kusunoki et al. (Catal. Comm. 6 2005 645-649) describe a Ru/C and ion exchange resin for conversion of glycerol in aqueous solution. Again their process however, results in low conversions of glycerol (0.9-12.9%). Still other processes are described, for example, in U.S. Pat. Nos. 7,928,148; 6,479,713; 6,291,725, or 5,354, 914, the contents of each are incorporated herein by reference in their entirety.

Some processes of hydrocracking complex mixtures of higher carbohydrates involve reacting reagents under alkaline conditions. According to some processes, the pH value of a resulting polyol product mixture, containing propylene glycol and ethylene glycol, is neutralized with a strong acid, such as $H_2SO_4$ or HCl, after the reaction is completed. This unfortunately can contribute to problems in subsequent purification. By introducing a strong acid (e.g., pH≤1.5 or 2.0), one protonates the salts of organic acids in the mixture.

Polyols produced by hydrogenolysis of bio-derived feedstock often comprise a mixture of several polyols having a lower average molecular weight than the starting material. One of the recognized problems in the conversion of polyols, such as sugars and glycerol to polyhydric alcohols, such as propylene glycol and ethylene glycol by hydrogenous or by hydrocracking results in formation of not only these alcohols, but also several other diol compounds, which reduces the purity of the desired component. These unwanted products are recovered along with propylene glycol and ethylene glycol, and include for example: 1,2-butanediol, 1,3-butanediol, 1,4-butanediol, 2,3-butanediol and 2,4-pentanediol. Such impurities of the polyol product, mixture (derivatives) present a problem for sale and use of the product.

Due to the similarity in boiling points, these diols are very difficult to separate from propylene glycol by distillation. Hence, the separation of substantially pure propylene glycol or ethylene glycol from these other polyhydric alcohols by ordinary rectification is difficult. For example, the butane diols (BDO), pentane diols (PDO) of various isomeric forms (e.g., 2, 3 BDO: 1, 3 PDO) are the most difficult to separate from propylene glycol using current distillation processes because their boiling point temperatures are very close to that of propylene glycol (i.e., 185° C.-189° C. The boiling points of many of these components are shown in Table A.

TABLE A

Polyols produced by Hydrocracking of Sorbitol

| Polyol | Weight Percent (%) | Boiling Point (° C.) |
|---|---|---|
| 2,3-Butanediol | 3.5 | 182 |
| Propylene glycol | 16.5 | 187 |
| 1,2-Butanediol | 2.0 | 192 |
| Ethylene glycol | 25.2 | 198 |
| 1,3-Butanediol | 2.7 | 206 |
| 2,3-Hexanediol | — | 206 |
| 1,2-Pentanediol | — | 210 |
| 1,4-Pentanediol | — | 220 |
| 1,4-Butanediol | 2.1 | 230 |
| 1,5-Pentanediol | 0.1 | 242 |
| Diethylene glycol | 2.2 | 245 |
| 1,6-Hexanediol | — | 250 |
| Triethylene glycol | 2.1 | 285 |
| Glycerol | 38.8 | 290 |
| 1,2,4-Butanetriol | 4.8 | 190/18 mm |

The differences in volatility of propylene glycol compared to 2,3-butanediol or 1,2 butanediol are very small. The relative volatility is so low that a large number of theoretical plates are required to produce high purity polyols. As shown in Tables B and C, the number of plates required to achieve 99% purity is very large, requiring the use of very tall distillation columns (55 trays for 2,3-Butanediol and 88 trays for 1,2-Butanediol) and high energy inputs.

TABLE B

Theoretical and Actual Plates Required vs. Relative volatility for Separation of Propylene Glycol and 2,3-Butanediol.

| Relative Volatility | Theoretical Plates | Actual Plates, 75% Efficiency |
|---|---|---|
| 1.25 | 41 | 55 |
| 1.35 | 31 | 42 |
| 1.45 | 25 | 34 |
| 1.50 | 23 | 31 |
| 1.70 | 18 | 24 |

TABLE C

Theoretical and Actual Plates Required vs. Relative volatility for Separation of Propylene Glycol and 1,2-Butanediol.

| Relative Volatility | Theoretical Plates | Actual Plates, 75% Efficiency |
|---|---|---|
| 1.15 | 66 | 88 |
| 1.5 | 23 | 31 |
| 2.0 | 14 | 19 |
| 3.0 | 9 | 12 |
| 3.5 | 8 | 11 |

Some approaches for separating and purifying a hydrogenolysis reaction mixture are discussed, for example, in commonly assigned U.S. Pat. No. 8,143,458, to Kalagias et al., and U.S. Patent Publication No. 2009/0120878A1 to Hilaly et al. U.S. Pat. No. 8,143,458 describes a process for separating ethylene glycol or propylene glycol from mixtures containing the ethylene glycol or the propylene glycol and other polyols using polar compounds by means of an addition of a polar solvent and extractive distillation. U.S. Patent Publication 2009/0120878A1 describes methods of separating butanediol compounds, particularly 1,2-butanediol and 2,3-butanediol from a mixture of polyhydric alcohols using a simulated moving bed chromatography as a means to achieve a purified, commercial grade bio-based propylene glycol. The contents of each of the foregoing patent documents are herein incorporated.

The prior art describes the difficulty of refining and purifying propylene glycol or ethylene glycol from a hydrogenolysis product mixture. A compounding difficulty however arises from the fact that in distilling the entire polyol product mixture to remove the impurities of other undesired polyhydric alcohols, additional reactions occur that give rise to aldehydes, ketones, esters and epoxides. Polyol products that can contain these compounds are commercially unacceptable in terms of the purity and quality of propylene glycol yielded. For example, in distilling out, epoxides such as propylene oxide and glycidol can be formed. These two epoxides in particular are of concern for certain established uses and commercially important applications of propylene glycol, at least, for the reason that these substances are listed under the State of California's "The Safe Drinking Water and Toxic Enforcement Act of 1986"—more commonly known as Proposition 65—as being known to California to cause cancer. Consequently, having a biobased, drop-in replacement propylene glycol for a petroleum-based or -derived propylene glycol will depend, for certain markets and end uses at least, on developing an economical process of separating polyethylene glycol and/or ethylene glycol from other polyhydric alcohols that also satisfactorily addresses this problem.

International Application Serial No. PCT/US2012/026728, the contents of which are incorporated herein by reference, proposes several methods for solving this further problem. For instance, the application describes a process for distilling a product mixture comprised of biobased propylene glycol, biobased ethylene glycol or a combination thereof and which further includes one or both of propylene oxide and glycidol, so that a distilled biobased glycol product stream is produced which is substantially free of both propylene oxide and glycidol. Epoxide removal is thus integrated into the refining process for a crude reaction product, to produce the desired biobased, commercially acceptable glycol product.

SUMMARY OF THE INVENTION

The present invention pertains in part, to a method for reducing contaminants in the production of a bio-derived glycol product of polyol hydrogenolysis, such as propylene glycol or ethylene glycol. The method involves: providing a renewable or bio-derived polyol feedstock; reacting said feedstock in a reactor to produce an aqueous product mixture, including one or both of propylene glycol and ethylene glycol with higher polyols; subjecting said reaction product mixture to ion-exclusion chromatography to separate and reduce impurities from an eluant fraction containing a desired product; and distilling the eluant fraction to yield a glycol (e.g., propylene glycol and/or ethylene glycol). One may further subject the reaction product to ion-exchange in addition to ion-exclusion chromatography.

In another aspect, the invention relates to a method of manufacturing propylene glycol and/or ethylene glycol. The method involves providing a biologically-derived feedstock of three, five, and six carbon sugars and/or sugar alcohols; converting the feedstock by hydrogenolysis to a reaction product mixture containing polyols (e.g., propylene glycol and/or ethylene glycol) and impurities; extracting and introducing the reaction product mixture into an ion-exclusion chromatography system to reduce impurities from an eluant fraction containing propylene glycol and/or ethylene glycol; distilling the eluant fraction through a distillation system having a first column that removes alcohols, a second column that removes water, a third column that removes unreacted components or organic components having higher boiling points than that of ethylene glycol, a fourth column that removes ethylene glycol, and a fifth column that removes epoxides, esters, $C_4$-$C_5$ and higher diols, residual water and propylene glycol.

We have found in relation to these aspects that removing organic acids and salts from a polyol hydrogenolysis product mixture prior to distilling the product mixture in order to recover a bioderived propylene glycol and/or ethylene glycol product eliminates a great majority of the byproducts, impurities, and other components that tend to cause problems in downstream distillation and purification of the bio-derived glycol products of polyol hydrogenolysis.

Additional features and advantages of the present purification process will be disclosed in the following detailed description. It is understood that both the foregoing summary and the following detailed description and examples are merely representative of the invention, and are intended to provide an overview for understanding the invention as claimed.

DETAILED DESCRIPTION OF THE INVENTION

Section 1

Definition of Terms

Before describing the present invention in detail, certain terms that have meanings generally understood by those of ordinary skill in the art are nevertheless defined herein to better distinguish nuances in meaning that may apply to different embodiments of the invention, it is understood that the definitions provided herein are intended to encompass the ordinary meaning understood in the art without limitation, unless such a meaning would be incompatible with the definitions provided herein, in which case the definitions provided control. As used in this specification and the appended claims, the singular forms "a," "an," and "the" include plural referents unless the context clearly dictates otherwise.

The terms "bio-derived," "biologically-derived," or "renewably-sourced" may be used interchangeably to refer to materials or a product whose carbon content originates from or is based upon biological products or renewable materials (including, but not limited to, plant animal and marine materials).

The term "eluant" refers to a mobile phase of fluid passed over a chromatographic bed material to accomplish sorbent separation.

The term "eluant reactant" refers to a mobile phase containing a species that acts both as a reactant for a chemical reaction and an eluant for either adsorptive/desorptive separation or chromatographic separation of chemical species. If eluant reactant is chemically converted to a product while serving as an eluant, the product will also be the eluant.

The term "raffinate" is a general term that refers to the liquid effluent or fraction resulting from a separation procedure and that does not contain the desired product (or products).

The terms "continuously operating" or "continuously separating" in reference to use of a sorbent chromatographic separation process means that the process is conducted indefinitely over time with an uninterrupted input of reactants and/or eluent(s), with an uninterrupted withdrawal of product and/or raffinate, and if elected, with art uninterrupted flow of bed preparation material. In this regard, both adsorptive/desorptive separation and chromatographic separation can be continuously operated, with the difference being that in adsorptive/desorptive separation there is some section of the chromatographic bed subject to disconnection from the series so that it can be treated with a discrete discontinuous change in eluent conditions.

Section 2

Description

Figure 1:
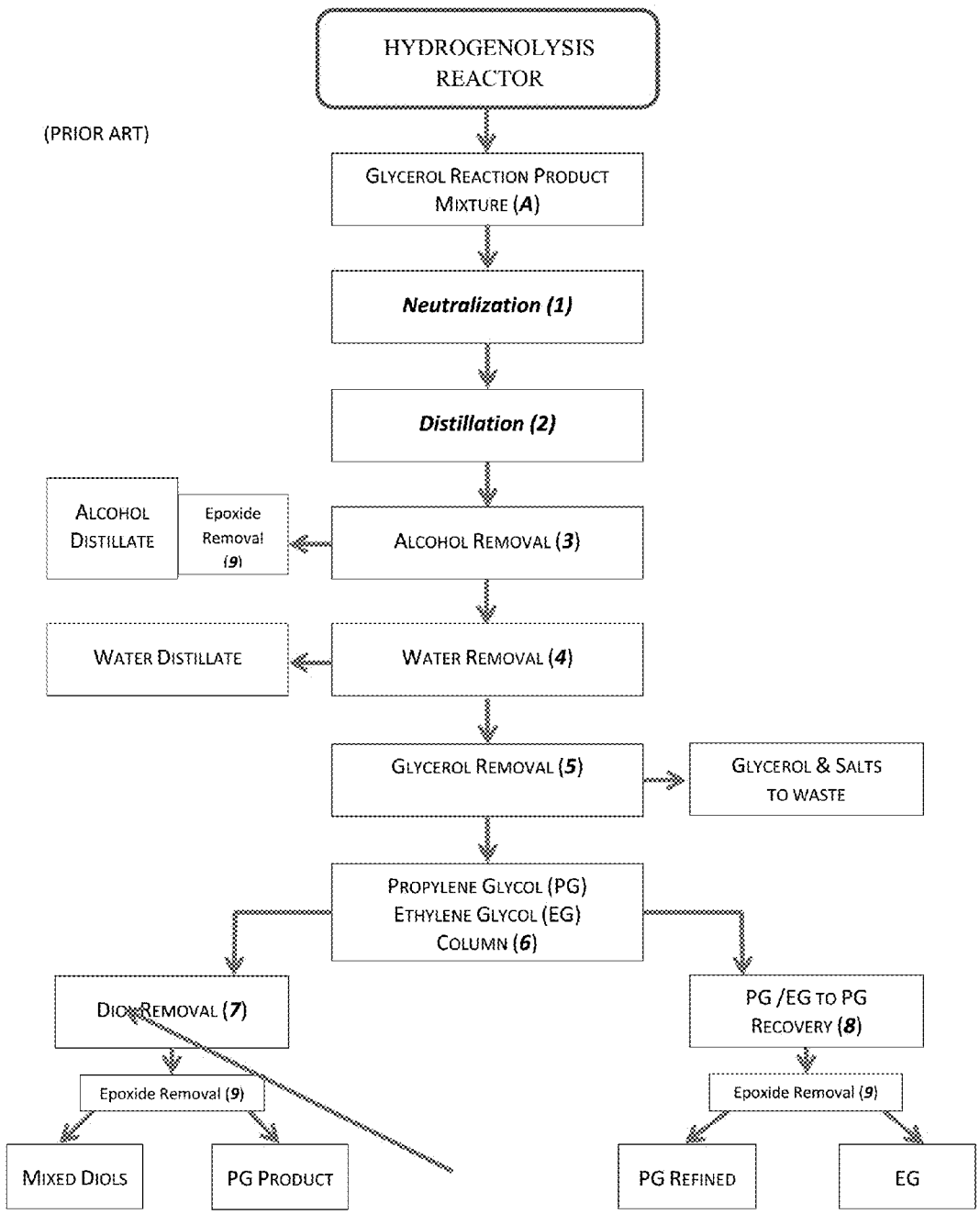
FIG. 1 is a schematic illustration of one embodiment of a post-hydrogenolysis process for purifying propylene glycol made from bio-based reagents according to International Application Serial No. PCT/US2012/026728/U.S. patent application Ser. No. 61/452,311, for purposes of comparison to the inventive process shown in FIG. 2.

One of the problematic issues with bio-derived propylene glycol production techniques has been difficulties in the downstream purification. FIG. 1 shows a schematic representation of steps involved in a conventional post-hydrogenolysis processing of glycol products made from bio-based reagents. (One may use, for instance, the process for preparing low molecular weight polyols from high molecular weight polyols in a hydrogenolysis reaction under elevated temperature and hydrogen pressure as described, in U.S. Pat. No. 6,291,725, or any of the other processes cited above.) Glycerol and a strong base are reacted together in the presence of hydrogen. The pH value of the resulting reaction product mixture (A) is neutralized with a strong acid (1), and the mixture is distilled (2). Each of the distillate tractions containing alcohol (3), water (4), glycerol (5), and the final polyol (i.e., propylene glycol, ethylene glycol (6), and diol products (7) is separated in turn in a number of distillations. The polyol product mixture (6) is further separated into the component propylene glycol and ethylene glycol in a PG recovery column (8). Conventional purification processes tend to allow the formation of impurities that lower the flashpoint. This makes the distillation separation more complicated. Also, in the conventional process after each of the separations, typically the distillate is filtered or further purified, and through these additional refining steps a not insignificant amount of the desired PG product may also be lost to the co-products. A separate step for removing epoxides (9) from each desired product stream means additional cost.

Moreover, in conventional PG distillation processes, epoxide formation occurs with the residual organic acid compounds present under the conditions experienced during distillation. One method for dealing with these compounds is to catalytically convert them into innocuous compounds (i.e. glycidol converts to glycerol, propylene oxide converts to propylene glycol). It is observed that catalyst, grade strong acid ion exchange resins, used in epoxide removal (9), such as depicted in FIG. 1, tend to degrade within, a short time of about a month. The need to replace or regenerate these ion-exchange resins often causes downtime in the product process, which can add to costs.

According to the present invention, we describe a process that can effectively either reduce or remove organic acids and salts that arise from hydrogenolysis of polyols, such as glycerol, sorbitol, xylitol, mannitol, iditol, etc. These organic acids and salts can promote the formation of reaction impurities and by-products. A feature of the present separation process is that the pH of the reaction product mixture is not neutralized. Rather the mixture maintains an alkaline or high pH value, saving costs associated with the use of acids to neutralize products from the reaction and reducing (or avoiding altogether) the need for epoxide removal measures from the desired product(s). (In conventional processes, the presence of organic acids and salts in the polyol product mixtures helps to catalyze formation of epoxides and other compounds during the distillation.) The present inventive process can be adopted for continuous separation of various impurities and by-products from a propylene glycol production stream. By removing certain organic acids and salts early in the process, a cleaner charge or distilland is provided for avoiding many of the undesired side reaction products, the overall distillation time may be shortened, and a more purified distillate may be generated at a higher total yield.

In its various embodiments, the present invention addresses the need for a bio-based glycol product that is compliant with the requirements of Proposition 65 and preferably substantially free of propylene oxide and glycidol. In one approach, the present invention addresses this difficulty by providing, according to a first aspect, a process for distilling a mixture containing propylene glycol, ethylene glycol, propylene oxide, glycidol and other monools and diols, such as a mixture obtained from the hydrogenolysis reaction with a sugar or sugar alcohol or with glycerol according to a method of the type described above.

The process involves taking a product mixture from a reactor, employing either ion-exclusion chromatography alone, or ion exclusion in combination with ion exchange to reduce or eliminate organic acids and salts from the resulting product mixture before the product mixture is introduced into distillation. This feature helps minimize the generation of various co-products, such as organic acids, epoxides, and diols, and simplify the downstream separation and purification for such co-products. In particular, the process involves reacting a renewable or bio-derived feedstock in a reactor to produce a product mixture containing propylene glycol, ethylene glycol or both, removing the product mixture without neutralization with acid, contacting the product mixture with an ion-exclusion resin to separate out organic acids and salts from the product mixture and yield a distillation feed including propylene glycol, ethylene glycol or both but having a reduced content of organic acids and salts. Subsequently, one can also subject the product mixture to an ion-exchange resin.

I

Replacing the acid neutralization step with ion-exclusion chromatography can reduce substantially or remove completely salts and organic acids in downstream distillations. Preferably all or substantially all of the salts are so removed, for example, at least about 85 percent, more preferably at least about 90 percent and most preferably more than about 96 percent of the salts are removed. In the conventional process shown schematically in FIG. 1, wherein salts and organic acids are not removed before distilling, the nature of the distillation process drives the equilibrium toward the free acid. The acid components tend to boil off into the distillate products leaving the bottom materials to have an increasing degree of alkalinity. Minimizing the issues of acidic distillate and basic bottoms products can improve greatly the purity and yield of co-products. Acids lead to aldehydes via dehydration, while basic pH conditions cause polymerization. Moreover, the salts have been found to contribute to the production of epoxides such as propylene oxide and glycidol in the distillation and refining of the aqueous reaction product. We have thus found that control of the organic acid and salt content of the distillation mixture can lead to multiple benefits.

Without the need for acid neutralization and with the substantial elimination of acids or salts before distillation, as well corrosion of piping or vessels or leaching of iron, molybdenum, nickel, etc. from conventional carbon or stainless steel storage vessels, or corrosion caused by organic acids in the overhead works of distillation equipment, can be avoided.

The omission of a neutralization step does not mean that pH control of the reaction product mixture is unimportant, though as explained above, the manner in which such pH control is accomplished (by removal of organic acids and salts through ion exclusion rather than neutralization through acidification) has a significant impact on product yields and purities. Excess acidity in the reaction mixture can lead to the formation of colorant and odorant compounds, such as aldehydes and ketones (e.g., propion-aldehyde and acetone odorants) or high-molecular weight polymers. These carbonyl compounds can condense to form colored polymers. Reducing the amount of carboxylic acid in the distilland will reduce the formation of carboxyl compounds that form colored compounds. The present process can reduce the opportunity for acid-catalyzed dehydration that generates odorants in the distillates. The demonstrable difference in the purity of product and benefits in the refining process between the different approaches for pH control can be seen in the accompanying Examples below.

Another advantage of the present process is that by removing the salts from the distilland, the glycerol column can work more efficiently at lower temperatures and with better recovery of glycerol than before when using a feedstock that had not been treated chromatographically. Without the acidic species being driven off in the distillate as in conventional processing, a more neutral pH in distillation column bottoms will tend to contribute less to base-catalyzed polymerization. Hence, one can avoid the need to heat the distillation column to ever higher temperatures to counteract, the viscosity of the salts and glyceride polymers (e.g., di- or triglycerols). One observes a reduction in viscosity in the bottoms product in the glycerol column.

Often hydrogenolysis reactors are not 100% efficient, and an amount of glycerol is not completely reacted; some residual amount of unreacted feedstock remains. The elimination of salts produces a relatively cleaner glycerol extraction in the glycerol-removal column (GRC) bottoms that can then be recycled directly back into the reaction. This feature enables one to reuse and save costs associated with starter materials.

The quality of distillate co-products is also improved with the present ion-exclusion chromatographic process. Using ion-exclusion chromatography without acid neutralization, up to about 98% of the co-product compounds can be removed for a cleaner distilland (i.e., has less byproduct content). Moreover, when the distilland is further purified in the subsequent distillation stream, the resulting propylene glycol product can have a higher level of purity achieved by means of a shortened distillation with less expenditure of energy and time in a simpler and more economic process than done conventionally.

Other advantages may include, for example, reducing salt-related fouling of the water-removal, column (WRC) packing; reduced fouling/pressure drops across the glycerol-removal column (GRC) bottoms or pumps; or reducing opportunities for formation of epoxides or of other impurities from dehydration products (e.g. acetone), which tend to lower the flashpoint of the volatiles.

II

Figure 2:
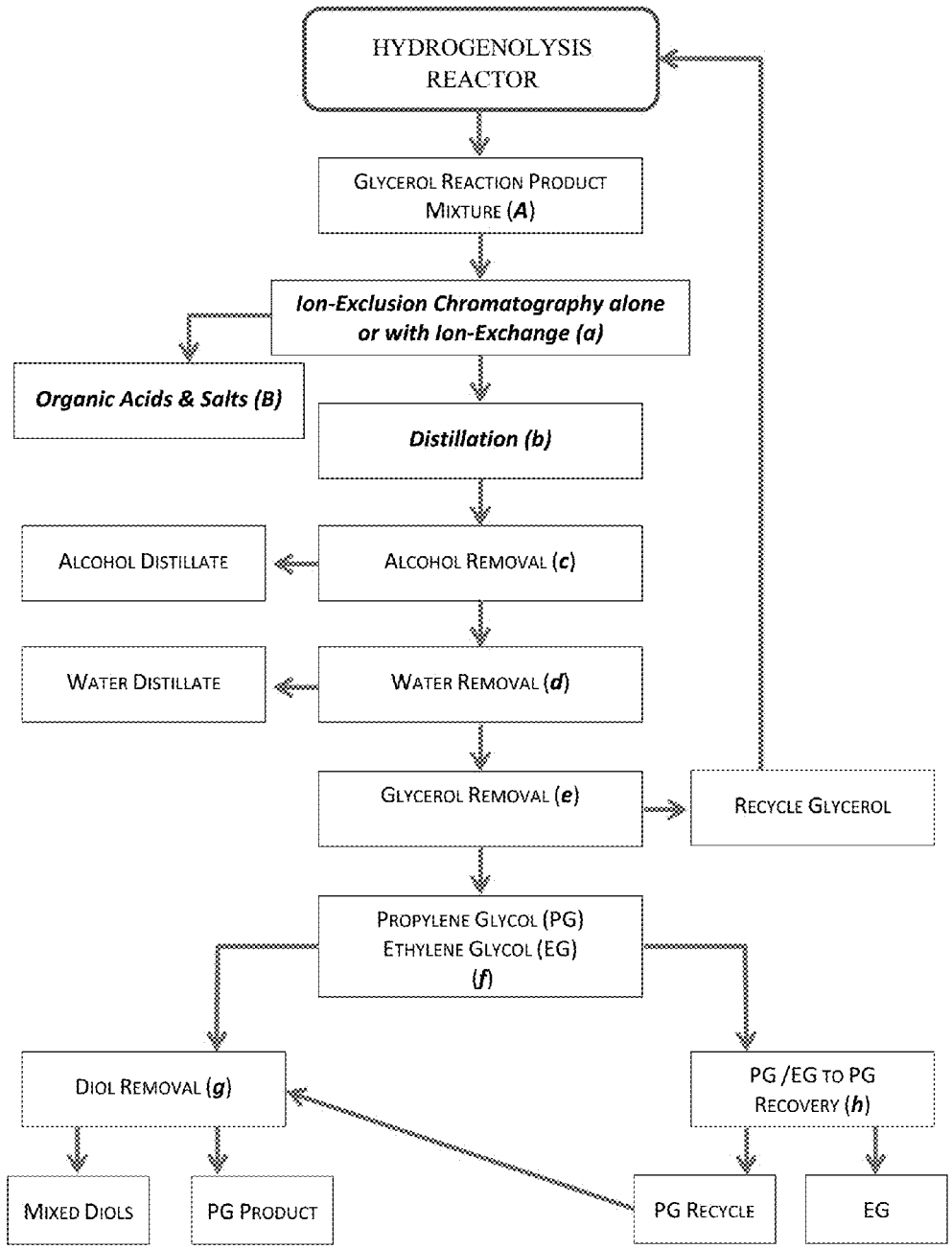
FIG. 2 is a schematic representation of a separation process according to an iteration of the present invention, in which a reaction mixture from a hydrogenolysis reactor is not neutralized with a strong acid, as in a process as shown in FIG. 1, but rather is subjected to either ion-exclusion chromatography alone or ion exclusion in combination with ion-exchange to remove organic acids and salts before the mixture is distilled as past of a glycol purification process.

FIG. 2 shows a schematic representation of an iteration of the present inventive process as compared to FIG. 1. The present process uses a preliminary separation to eliminate or reduce the amounts of contaminants present, especially salts, in the reaction product mixture (A), in contrast to the conventional process, the pH value of the reaction mixture containing propylene glycol is maintained initially at an alkaline level, and not neutralized with an acid. Avoidance of pH neutralization minimizes organic acids and salt ions present in the reaction mixture. The reaction mixture is subject to either ion-exclusion chromatography alone or in combination with ion-exchange to remove organic acids and salts from the mixture (a). The ion exchange could be employed after an ion exclusion step. This increases the raw purity of the distilland and enables one to simplify the subsequent distillation process. In other words, these steps can help to eliminate or reduce the amounts of byproducts, contaminants, and other processing issues that can develop in subsequent distillation streams. By first separating much of the undesired organic acids and salts (B) from the raw reaction product mixture (A), one also lowers the pH from basic to neutral without the need to titrate with acid. This also can help in the control of pH in the subsequent distillation (b), further minimizing the generation of and side effects of co-products that will reduce the purify of the propylene or ethylene glycol product. Additionally, the new process reduces formation of diols and other byproducts in distillation and other impurities in the finished PG product. Since some diol isomers have a vaporization temperature very close to that of propylene glycol, separation of the two species is very difficult by means of distillation.

Although the product mixture has an alkaline pH value between about 8.0 and about 12.0 when extracted from the reactor, the product mixture can be introduced into a simulated-moving bed ion-exclusion chromatography system without first neutralizing with an acid. The eluent fraction can be introduced directly from the chromatography system to a distillation system (b). The distillation system (b) comprises a first column (c) that removes alcohols, a second column (d) that removes water, a third column (e) that removes unreacted components or organic components having higher boiling points than that of ethylene glycol, a fourth column (f) that removes ethylene glycol, and a fifth column (g) that removes epoxides, esters, $C_4$, $C_5$ and higher diols, residual wafer, and propylene glycol. The bottoms content (e.g., glycerol) from the third distillation column (e) can be recycled directly back into the reactor; hence, providing another cost and materials savings and reduction of waste. The propylene glycol and ethylene glycol species can be further separated in another column (h).

The ion-exclusion chromatography can use a resin selected from a gel-type strong acid cation (SAC) resin (in the sodium form), gel-type strong base anion (SBA) resin, or macroporous resin.

The reaction product mixture can be introduced into a continuous ion-exclusion chromatography system to reduce impurities from an eluant fraction containing propylene glycol and/or ethylene glycol. The impurities tend to include organic acids, salts, diols, and unreacted feedstock. The eluant fraction is distilled through a distillation system having a first column that removes alcohols, a second column that removes water, a third column that removes unreacted components or organic components having higher boiling points than that, of ethylene glycol, a fourth column that removes ethylene glycol, and a fifth column that removes epoxides, esters, $C_4$-$C_5$ and higher diols, residual water and propylene glycol. Distillation can be performed either according to conventional processes and temperature conditions or as described in U.S. Patent Application Publication No. 2008/0274019, the contents are incorporated herein by reference.

According to the invention, impurities are designed to be carried out the top of each column in the last three distillations, and a desired main product is designed to be a bottoms product. For example, discoloring agents tend to be lighter molecules which are distilled off, while the heavier PG remains.

Because no distiller is 100% efficient, over the distillation process a small amount of PG conventionally is lost to the top product. As the amount of PG loss from each step of the purification process is minimized with the reduction of salts and acids, the process should enhance the recovery of PG in each distillation step. Hence, the present inventive process can increase the overall yield of propylene glycol.

III

Ion-exclusion chromatography (IEC) and ion-exchange (IX) both work very well to remove ionic species from non-ionic species within a liquid mixture. They are not the same, however, each having certain advantages and limitations. In the present process, we contemplate that IEC as the primary salt and organic acid removing technique while IX is a secondary technique, which can complement each other. In some embodiments, the two techniques can be used in sequence depending on the quality of product desired.

As the examples in Part D of Section 3 show, one can derive considerable cost savings when processing in high volumes reaction product feedstock that contains high salt content. The results in the examples indicate a more economical way of processing and removing the salt load from reaction product feedstock. As shown in Example 3, the resin load for ion exchange was about 122 times greater than for the IEC using both SAC and WBA resins at high salt loads. This significantly higher resin requirement of ion exchange and the accompanying large quantities of chemicals needed to regenerate the resins make the ion exchange technique prohibitively expensive at higher salt concentrations; whereas, IEC is more efficient and cost effective at removing high salt loads.

Hence, according to the present invention, it is desirable to process reaction product feeds first using IEC, and then optionally using ion exchange if a product of more pure quality is desired.

It is unexpected that separations by means of ion exclusion chromatographic alone or with ion exchange combined enables one to reduce some of the diols with longer carbon-chain (e.g., C4-C6) from the reaction mixture. This is because ion-exclusion and ion-exchange techniques are usually targeted at ionic compounds, which, the techniques work very well to remove. Diols, however, are principally uncharged species. Although ion exchange resins can remove some organic materials, this is typically due to adsorption, requiring some type of regeneration solvent or chemical, rather than simple retardation chromatography as appears to be occurring in the present process.

A. Ion Exclusion Chromatography (IEC)

Separation and removal of organic acid salts may be accomplished by ion exclusion chromatography, using resins known to those skilled in the art as suited for this purpose, for example, any of the various sodium or calcium form, strong cation exchange styrene/polystyrene-divinylbenzene copolymer resins, such as those available from The Dow Chemical Company under the trade designations DOWEX 99/320, DOWEX 99/290, DOWEX N406, N306 AND N606, AMBERLITE CR1310, CR1320, C20N and IR 120, and AMBERJET 1000Na, 1300Na and 1500 Na, from Mitsubishi Chemical Company under the trade designations UBK550, UBK510L and UBK530, from The Purolite Company under the trade designations C100, PCR145, PCR450, PCR642, PCR732 and PCR833 or from a number of other manufacturers. Simulated moving bed chromatography methods have been found useful for essentially continuously removing the salts, as exemplified below. Ion exclusion can remove the great majority of cations and anions from reaction product mixture. Unlike with ion-exchange resins, an ion exclusion resin does not require regeneration since the feed contains enough cations (i.e., sodium) to keep the resin in the proper ionic form.

Ion exclusion chromatography involves an adsorbent material that is saturated with the same mobile ions (cationic or anionic) as are present in the sample (i.e., feed), thus repelling the similar sample ions. Ion exclusion chromatography is based on ion exchange resins beds acting as a charged solid separation medium. The ionic components of the processed fluid have different electrical affinities to this medium than the non-ionic compounds, and are, as a result, differently retained by the resins thanks to these different affinities. Therefore, by elation, these components can be recovered separately at the outlet of the resins bed. The characteristic feature of the IEC technique is that the electric charge sign of the dissociated functional groups of the ion-exchange resin is the same as the electric charge sign of the analyzed ionic compound. It follows that samples of negatively charged ions, e.g., dissociated acidic compounds, are separated on cation exchange resins with anionic functional groups. The same columns can be used in IEC and in ion exchange chromatography. For the specific requirements of IEC, a large ion exchange capacity is preferred. (See generally, Bronislaw K. Glód, "Ion Exclusion Chromatography: Parameters Influencing Retention," NEUROCHEMICAL RESEARCH, Vol. 22, No. 10, 1997, pp. 1237-1248, contents incorporated herein by reference.)

As a feature of the present invention, ion exclusion chromatography uses a reduction of mobile ions within an ion exchange resin due to the presence of fixed ions of the same charge as the mobile ions (i.e., Donnan exclusion) to carry out the separation between ionic compounds and non-ionic compounds. In this instance, the process uses strong acid cation (SAC) resin in the sodium (Na+) form to separate sodium hydroxide (NaOH), sodium lactate, and other assorted sodium salts from propylene glycol reactor product. Using Donnan exclusion, the resin, in the Na+ form, prohibits the movement of sodium compounds into and through the individual resin beads, causing them to go around the beads and migrate through the column more quickly than the non-ionic material which is free to move through the individual resin beads.

Ion exclusion chromatography can employ either SAC or strong base anion (SBA) resins depending on the makeup of the salts to be separated. If the salt is predominantly sodium, for instance, with mixed anionic counter-ions then SAC resin ion exclusion is preferred; if the salt is predominantly, sulfate, for instance, with a mixture of cation counter-ions then SBA ion exclusion in the sulfate form may be desired.

To increase column capacity, dimensions and functional group concentration in the support are maximized and strong ion-exchange (anion- or cation-exchanger) resins are used: however, true ion-exchange reactions are not involved. The usual supports are based on the micro-porous (gel type) styrene and divinylbenzene copolymers, resulting in IEC columns that are typically micro-porous, totally sulfonated cation exchange resins with high exchange capacities. The resin is prepared by the catalytic polymerization of a mixture of styrene and divinylbenzene emulsified in water. This reaction yields spherical beads of crosslinked resin, characterized by the divinylbenzene concentration in the reaction mixture.

Ion-exclusion chromatography, like other chromatographic techniques, is classified according to the primary mechanism of solute retention. In addition, ion exclusion permits hydrophobic adsorption on the resin network (as in reversed phase chromatography), size exclusion, the effect of functional group screening in the analyzed sample, normal phase retention, and van der Waals and polar interactions of the sample compound with the support. The major advantage of IEC lies in its ability to process samples having very complex compositions. It was found that even injections of samples of mustard or wines do not influence the long term effectiveness of the column for the separation of the organic acids in those samples.

Ion exclusion chromatography offers a proven economical advantage to the use of conventional fixed bed ion exchange resin systems, when dealing with feed materials with high (>2000 ppm) salt loads. Advantageous to the present refining process, IEC does not generate large quantities of regenerant waste, which can be a problem, as IEC avoids and uses no chemicals for regeneration and is simpler to operate. Further, this technology can economically handle large concentrations of salt (>75,000 ppm, 7.5%), whereas ion exchange purification tends to become uneconomical at higher salt levels, for example, over about 1500-2000 ppm.

B. Ion-Exchange (IX)

Ion exchange refers to a technique in which a solid phase of the resin with its associated ionic form interacts with the solution around it in such a way as to exchange the ions on the solid phase of the resin with the ions in solution. It is this second type of ion exchange technique that may be employed in combination with ion exclusion chromatography in some iterations of the present invention.

When the ion exchange resin is exhausted and breakthrough occurs (i.e., when effluent salt content, as monitored by conductivity, becomes above a desired level), the resin requires chemical regeneration. This regeneration step requires a chemical treatment, (acid for the strong acid cation (SAC) resin and caustic for the weak base anion (WBA) resin) slightly larger (~10%) than the ionic load removed during the service cycle.

Although some ion exchange resin beds are effective at removing epoxides and organic acids from byproduct streams, these resin beds do not protect upstream piping and equipment against corrosion, nor can they prevent glycol polymerization from the residual high salt concentrations in the distillation bottoms. Hence, the use of IX in combination with IEC would be a great improvement to remove all of the impurities early in the PG production process.

Advantages of ion exchange technology that, complements IEC include an ability of ion exchange to economically reduce concentrations of salt (starting at 1500-2000 ppm) to single digit ppm levels, while IEC cannot. Ion exchange processing adds little if any dilution to the liquid stream, while IEC requires large quantities of water for elation, which increases the water load and causes product dilution.

As used herein, ion-exchange chromatography and ion-exchange (IX) are not the same thing. Ion-exchange chromatography relies on ion-exchange but is still carried out chromatographically, by use of pH gradient, or reliance on dissimilar affinity of compounds in feed as in the separation of citric from hydrochloric acid—due to the large selectivity compounds exchanging and forming the ion-exchange hand toward the top of the column and the lower selectivity compounds forming the band toward the bottom of the column, causing separation in the column effluent.

After the treatment, one can achieve in the product mixture an amount of propylene glycol at a high concentration of about 85% or greater. Typically, the separation yields about 90% or greater propylene glycol content. After this "cleaner" reaction mixture is eluted from the chromatographic column, distillation can be used to remove any remaining impurities.

IV

Continuous Processing

The present approach to producing propylene glycol more simply, at less cost, and potentially maximizing the recovery of other cleaner co-products, such as alcohols, glycerol, or esters, can be achieved by means of various production procedures. We envision, however, for practicality and efficient, results use of simulated moving bed chromatography. Simulated moving bed (SMB) chromatography is a continuous purification technique that has higher throughput and requires less resin, and therefore less solvent than regular hatch chromatography. Even for difficult separations, if can achieve high yield and high purity at a reasonable production rate. SMB technique is used to separate particles and/or chemical compounds that could prove to be difficult or impossible to resolve otherwise. SMB chromatography is based on a flow of liquid (mobile phase) moving countercurrent to a constant flow of solid (stationary phase). Countercurrent flow enhances the potential for the separation and, hence, makes the separation process more efficient. It also permits a continuous flow of feed material to be separated, which improves the throughput of the equipment compared to batch processing. SMB chromatography is achieved by the use of a multiplicity of columns in series and a complex valve arrangement; which provides for sample and solvent feed, and also analyte and waste takeoff at appropriate locations of any column. Typically, in other words, the columns are arranged in a circle or ring formation made up of four sections with one or more columns in each section. The inlet and outlet positions, relative to each column, are switched at regular intervals in the opposite direction of the fluid flow, thus simulating counter-current movement of columns. This is done by either a rotating valve, multiple valve assembly, either with stationary columns; or by mounting the columns on a carousel and continuously rotating the carousel counter-current to the fluid flow.

In the context of the present invention, a polyol hydrogenolysis reaction product mixture would be introduced into a simulated-moving bed ion-exclusion chromatography system without neutralization with acid. When affinity differences between molecules are very small, it is sometimes not possible to improve resolution via mobile- or stationary-phase changes. In these cases, the multi-pass approach of SMB can separate mixtures of those compounds by allowing their small retention time differences to accumulate.

Figure 5:
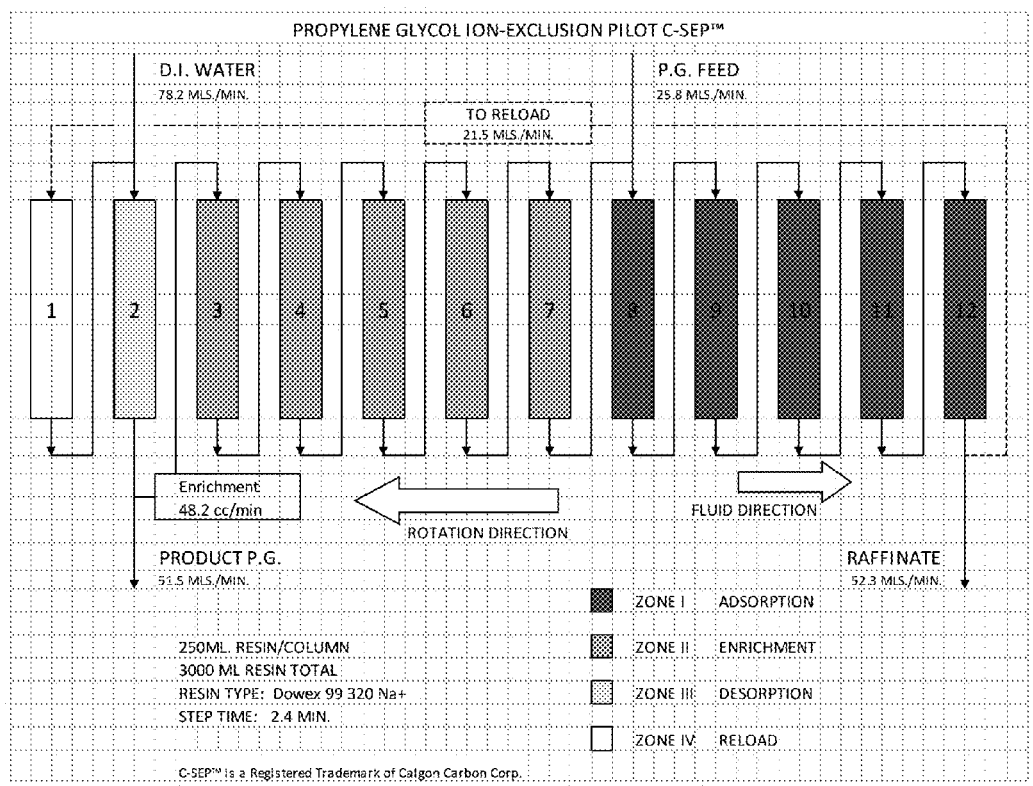
FIG. 5 is a schematic representation of a continuous simulated-moving bed (SMB) chromatographic apparatus that can be adapted for the present invention.

FIG. 5 shows a schematic representation of a simulated-moving-bed chromatographic apparatus as used to demonstrate the present invention in one iteration, and the relative direction of fluid flow and opposing direction of apparatus rotation. As indicated in the figure, resin adsorption occurs in Zone I enrichment in Zone II material desorption in Zone III, and reload in Zone IV. Sections I and IV handle "cleaning." The flow rates in Sections II and III are import because in these zones separation of the products occurs. Mobile phase exiting Section IV can be directly recycled back to Section I. The solid resin is regenerated by desorbing the more retained compound with a high flow rate so the complete column can be "moved" into Section IV. The figure shows along its course the relative elation of the various organic acids, salts, polyols, and other impurities from the propylene glycol in the reaction mixture.

In any simulated moving bed chromatographic apparatus the chromatographic bed material contained in the apparatus is conceptually divided into zones, where each zone may be distinguished from the other zones by the fluid flow in the chromatographic bed material in that zone. Zones may also be distinguished, for example, by the influent introduced or the effluent withdrawn in the zone or the dominant function that occurs within the zone. In certain embodiments where different fluids are applied in different zones, a gradient is established with increasing content of a first fluid and decreasing content of the second fluid and vice a versa in the opposite direction with respect to the position of the input zones.

In the typical simulated moving bed apparatus, the plurality of interconnected chromatographic bed segments are arranged in a sequential series and fluid ports are provided so that, a feedstock, eluent or other mobile phase material may be introduced to, or withdrawn from, any selected segment or position in the apparatus. An arrangement of valves at the top and bottom of each segment directs the flow of fluids into and out of any number of interconnected segments in the same or different zones at flow rates that can be independently controlled. The column segments can be arranged on a carousel type configuration that, cycles the column segments in a circular movement of positions in discrete steps over the course of the cycle, in this construction, the ports in contact with the column segments at the top and bottom of each segment are stationary, so that the column segments cycle in a circular movement with respect to the stationary port. In a complete cycle, each column segment passes through each different position and set of stationary ports where different predominant functions are occurring. The function occurring at any given position remains constant and therefore the position of the segment conceptually designates its zone. In an alternative to the carousel construction, the column segments are stationary and the ports in contact with the column, segments at the top and bottom of each column segment cycle in a circular movement with respect to the column segments. In a complete cycle, the movement of the ports causes each column segment to pass through each different position where different predominant functions are occurring. The function occurring at any given position remains constant and therefore the position of the segment conceptually designates its zone.

At industrial scale an SMB chromatographic separator is operated continuously, requiring less resin and less solvent than batch chromatography. The continuous operation facilitates operation control and integration into production plants. The present inventive process was unexpected in that SMB usually has been considered not to be suited for purifications that involve in particular the isolation of an intermediately binding single component or fraction out of a multicomponent mixture, when using isocratic elation.

In the present invention, we have investigated gel type strong acid cation (SAC) resins in the sodium form, but other macroporous resins can work as well. Gel type strong base anion (SBA) resins in the feed counter ion form (mixed organic/mineral acids) also can work well, but they tend to involve a more difficult process than the SAC resin process. Also, SBA resins have lower maximum temperature ratings and tend to lose functionality more quickly than their cationic counterparts; hence, SAC systems are more practical.

The resins range in size from about 220 microns to about 700 microns mean size. The typical pore size for a gel type resin is about 20-30 angstroms. Column packing can play a part in success or failure of this operation, as poor column packing can lead to voids within the bed or channeling of flows through the bed. Typically, the resin is prepared as aqueous slurry and then poured or pumped into the columns.

The chromatographic resins that can be used in the present inventive process are commercially available from a number of manufacturers (e.g., Carbochem, Inc. (Ardmore, Pa., USA). Dow Chemical Inc., Finex Oy (Kotka, Finland), Lanxess Corporation, Mitsubishi Chemical Corporation, Furolite Corporation, or Thermax Ltd. (Pane, India)). For instance, one can use an ion exchange resin such as a strong acid cation styrene-divinylbenzene (gel) sulfonate functional group with 300-350 µm volume median diameter, and 1.2-1.5 g/mL particle density (e.g., DOWEX™ MONOSPHERE™ 99 K/320 or Ca/320, Mitsubishi DIAION®UBKSSS a styrene-DVB (gel) with 200-240 µm particle size).

Section 3

Examples

In the following examples, an aqueous, polyol-containing product mixture is retrieved from the hydrogenolysis conversion of biologically-derived carbohydrate feedstock. Depending on the starting material employed, the manufacturing process converts glycerol, to a glycol. The glycerol is reacted with a metal catalyst in the presence of hydrogen, and a strong base is used to promote the reaction. The reactor product is pH~11 upon reaction completion; hence, the organic acids are largely present as sodium lactate, sodium formate, etc.

The product mixture is subjected to ion-exclusion chromatography to separate and reduce impurities from an eluant fraction containing a desired product, and distilling said eluant fraction to yield propylene glycol and/or ethylene glycol. Pulse tests show that separation of sodium salts, for example, from propylene glycol can work well while the implementation of this method using SMB technology will maximize throughput and consequently minimize capital requirement.

Figure 3:
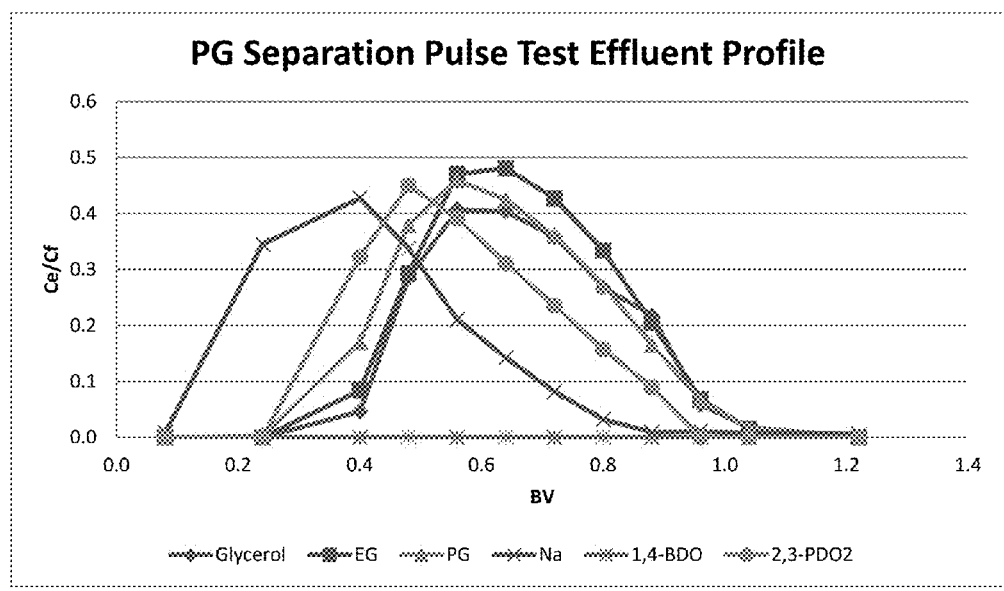
FIG. 3 is a pulse test illustrating ion-exclusion chromatographic separation of a propylene glycol-containing mixture performed according to an embodiment of the present invention.
Figure 4A:
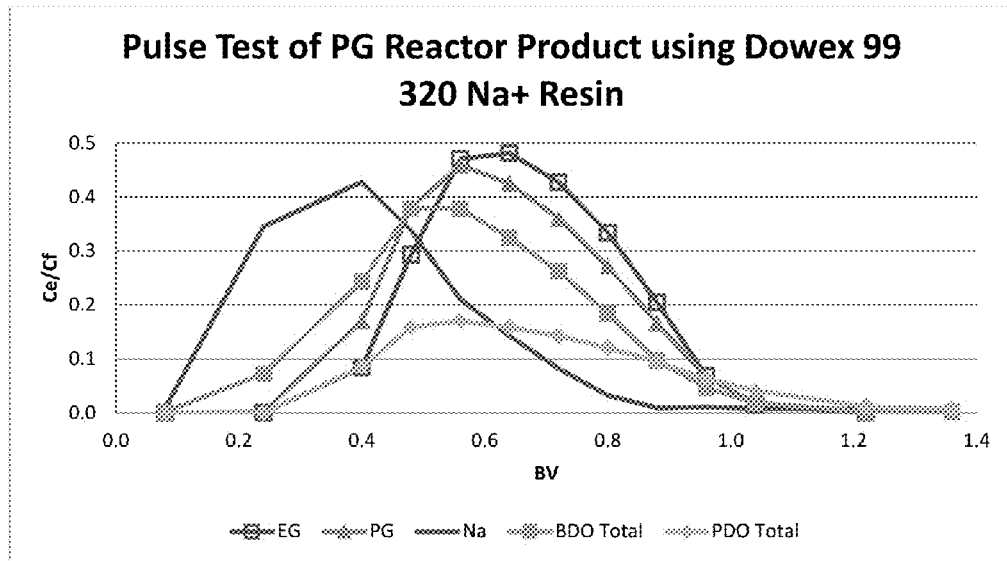
FIGS. 4A and 4B are other pulse tests according to an embodiment of the present invention.
Figure 4B:
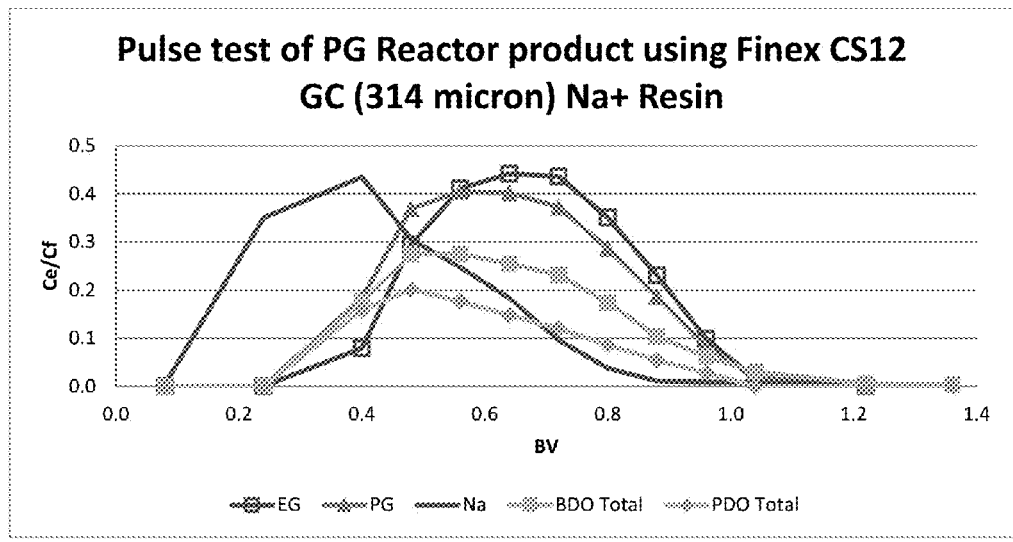

FIG. 3 shows a pulse test representative separation of effluent in which sodium is separated early in elusion. FIGS. 4A and 4B show similar elusions of reactor products using two particular commercial resins, DOWEX 99 (320) and Finex CS12 GC314, respectively, from Dow Chemical Inc. and Finex Oy (Kotka, Finland).

The pulse test procedure involves setting up a column and loading with desired adsorbent stationary phase, and conditioning the stationary phase appropriately for the separation to be carried out. This is typically a resin or gel matrix consisting of styrene divinyl benzene, agarose or cellulose beads with covalently bonded charged functional groups. The test begins with the introduction of a sample, onto the top of a column a sample loop of known volume. The sample is then allowed to flow into the top portion of the adsorbent bed, until even with the top of the bed. A mobile phase is introduced into the column, and the mobile phase carries the sample down through the column that contains the stationary phase material. In the case of ion-exclusion chromatography the target analytes (anions or cations) are excluded from going through the beads due to Donnan exclusion and therefore move more quickly through the resin bed. The non-ionic compounds are allowed to migrate through the resin causing them to move more slowly through the stationary phase, causing the two groups of compounds to be separated.

According to an embodiment of the present method, the simulated moving bed chromatography apparatus is arranged in a 1-1-5-5 configuration. Zone I is an adsorption zone; Zone II is an enrichment zone; Zone III is a desorption zone, and Zone IV is a reload zone (FIG. 5). The SMB apparatus contains 12 columns on a carousel, and provisions for rotating the columns in the direction opposite the flow of fluid at defined intervals, called the "Step Time", The step time is about 2.4 minutes.

Zone I (the Adsorption Zone) is defined by feed inlet and raffinate discharge ports. There are 5 columns in this zone (columns 8-12, shown in FIG. 5). Propylene Glycol (PC) feed (product of hydrogenolysis reaction) was applied continuously in the adsorption zone at 25.8 ml/min, joining the flow of recycled product in the SMB. The sodium salts were excluded from interaction with the resin in this zone and were continuously passed out of the SMB unit at the end of Zone I as "Raffinate" containing >93% of the sodium salts. The primary purpose of this zone was to allow sodium salts the opportunity to move through the bed leaving the non-ionic species (i.e. PCs, EG, glycerol) behind.

Zone II (the Enrichment zone) is a zone defined by product discharge and teed inlet ports (columns 3-7 shown in FIG. 5). The flow in this zone is about 48.2 ml/minute and there are 5 columns in this zone. The primary purposes of this zone are to a) ensure adequate driving force (through zone flow) for the salt to be discharged from zone, and b) increase the net concentration and purity of PG prior to being discharged front product, outlet. This increases the salt rejection and consequently the product purity.

Zone III (the Desorption zone) is a zone defined by the elation (deionized (DI) water) inlet and the product discharge port (column 2 shown in FIG. 5). There is 1 column in this zone. The primary purpose of this zone was to strip the non-ionic species from the resin. The DI water was pumped into this zone at 78.2 ml/minute, and it stripped the resin of glycerol EG and PG left from Zone II. At the end of the desorption zone, an effluent enriched in PG and nearly depleted of sodium salts was continuously elated from the SMB and allowed to pass out of the SMB as an effluent labeled "Product".

Zone IV (the Reload Zone) is the zone defined by the raffinate discharge and DI water inlet ports (column 1 in FIG. 5). There is 1 column in this zone. The primary purpose of this zone, in this application, is to prepare the column for the Adsorption zone. This zone also helps to decrease the volume of desorbent required to push the respective wave fronts through the system. The flow in this zone was 21.5 ml/minute, which is sufficient to displace the void fraction DI water from the column.

Using a C-SEP™ type (Calgon Carbon Corp.) continuous SMB system configured according to that shown in accompanying FIG. 5, a number of 250 ml resin columns, totaling about 3,000 ml of resin, is employed to separate the various component species in the reaction mixture. The step time is about 2.4 minutes. The PG-containing feed is introduced to column number 8 at about 25.8 ml/min., the mixture is eluted with de-ionized water at a flow rate of about 78.2 ml/min., and the organic acids and salt ions are sent to the raffinate at about 52.3 ml/min. The cleaned PG-containing mixture with salts removed is eluted at about 51.5 ml/min. If was observed that during the ion-exclusion step the concentration of BDO/PDO in the product was decreased as well. Data related to the BDO/PDO reduction using this method can be seen in Table 2, below.

tage of a SMB-based system enables manufacturers to apply a continuous feedstock flow info and product extraction out from the reactor and reaction product purification process. For purposes of PG production, the mobile phase is deionized water (DIW).

B. Chromatographic Resin is Conditioned in Preparation for Testing According to the Following:

Load 100 mLs of desired resin (prepared as slurry in deionized (DI) water) into a jacketed glass column and remove any air bubbles in the resin bed. Rinse the resin with approximately 5 bed volumes (BV) of DI water. Condition with approximately 10 BV of 5% hydrochloric acid, and follow with 5 BV of DI water. Next, run 10 BV of 5% sodium hydroxide through the resin, which converts to the sodium form, and chase with 10 BV of DI water. The resin is now ready for testing.

C. Pulse Test Procedure:

After resin is conditioned, open valve on top of column for remove top cap), then lower liquid level until even with top of resin bed. Add a poise of feed material (PG Reactor Product) and again lower liquid level to top of resin bed. Add 1-2 mLs, of eluent and close valve on top or replace top cap. Start elution flow at desired rate and begin fraction collection. Submit the samples for glycerol and sodium analysis.

TABLE 2

Reduction of Butane and Pentane Diols in Propylene Glycol using Ion-Exclusion Chromatography.

| Sample Id | 2-3 BDO (1) | 2-3 BDO (2) | 1-3 PDO | 1-2 BDO | 2-3 PeDO (1) | 2-3 PeDO (2) | PG | BDO/ PG (%) | PDO/ PG (%) |
|---|---|---|---|---|---|---|---|---|---|
| 9-12 13.15 PG prod | 0.66 | 0.64 | <0.05 | 0.19 | 0.09 | 0.10 | 130.00 | 1.000% | 0.146% |
| 9-12 13.15 PG raff ave | 0.08 | 0.11 | <0.05 | <0.05 | 0.03 | 0.02 | 8.00 | 2.38% | 0.625% |

Results are in g/kg

Ion-exclusion chromatography has worked well as a means of separating sodium salts (both mineral and organic), along with residual sodium hydroxide, from the propylene glycol. This separation is very important because organic acids cause many product, qualify and operational issues as they tend to migrate through the distillation process and react to form side products. In testing simulated moving bed (SMB) chromatography, we have discovered that removal of the contaminants earlier in the process before introducing the reaction product into distillation not only dramatically decreased the sodium salts but also reduced diol (BDO/PDO) content as well. Initial results suggest, that an amount of about 0.01-0.80 g/kg (e.g., 0.1-0.25 g/kg, 0.2-0.45 g/kg, 0.5-75 g/kg, 0.01-75 g/kg) of BDO and/or PDO can be reduced per kilogram of propylene glycol recovered. The separation of the BDO and/PDO from propylene glycol at this stage of purification is likely have great economic advantage for manufacturers in the renewable propylene glycol market.

A. Examples of Propylene Glycol Ion-Exclusion pulse Tests for Resin Screening

In a series of tests, we determine that separation of organic acids and salts from propylene glycol by means of ion-exclusion chromatography can effectively reduce the presence of butane-diols (BDO) and pentane-diols (PDO) in the reactor product. An ion-exclusion resin is run in a sodium form, since sodium is the predominant form in the salt. This work is specifically directed at the BDO/PDO reduction during this salt reduction ion-exclusion operation.

The ion exclusion resins used are: DOWEX 99 (320); Finex CS12 GC314; Finex CS11 GC323.

Butanediols and pentadiols are non-polar species, which can be separated using a polar phase compound. An advan- Fraction Collecting:

Collect fractions (8 mL fraction size) every 2 minutes.
Operating Conditions:
Chromatographic Column Temperature: 50° C.
Feed: PG/BDO/standard PG reactor product mixed 50:50
Feed Rate: 4 mls/min.
Pulse size: 20 mLs
Eluent: Deionized (DI) water Table 3, summarizes the range of product conversion (%), yield (wt. %), and selectivity (mole %) for the production of propylene glycol produced from hydrogenation of bio-derived feedstock in a first group of samples.

TABLE 3

|  | Range | Average for long run |
|---|---|---|
| Conversion, % | 88.2-95.5 | 90.0 |
| Yield, wt % | 63.5-72.0 | 67.2 |
| Selectivity, mole % | 86.5-91.3 | 90.5 |

Table 4 presents the range of product conversion (%), yield wt. %), and selectivity (mole %) for a second group of sample product.

TABLE 4

|  | Range | Average across 17 runs |
|---|---|---|
| Conversion, % | 93.7-98.4 | 96.4 |
| Yield, wt % | 63.8-70.2 | 67.7 |
| Selectivity, mole % | 80.7-88.1 | 85.0 |

Table 5, summaries the amounts of component species derived from reactor products in two representative examples.

TABLE 5

| Ex. | TOS (h) | T. (° C.) | Gly. | PG | EG | 1,2-BDO | 2,3-BDO | 2,3-PeDO | MeOH | EtOH | LA | FA | GA | AA |
|---|---|---|---|---|---|---|---|---|---|---|---|---|---|---|
| 1 | 67 | 205 | 25.8 | 263 | 17.3 | 0.27 | 1.90 | 0.33 | 6.30 | 0.32 | 4.53 | 0.28 | 0.18 | 1.36 |
| 2 | 934 | 205 | 23.2 | 281 | 16.9 | 0.21 | 1.57 | 0.21 | 6.32 | 0.26 | 4.19 | 0.20 | 0.10 | 0.19 |

Gly = glycerol, LA = Lactic Acid, FA = Formic Acid, GA = Glycolic Acid, AA = Acetic Acid
All values in g/kg.

Table 6, summarizes product analysis from a sample propylene glycol-containing feedstock, as an example of effective removal of organic acids and salt by means of ion exclusion separation. From an initial sodium content of more than 1600 ppm, sodium content is reduced to less than 35 ppm, which is an effect reduction of about 98%, to about 2% of initial levels. The overall amounts of various organic acids are also significantly reduced, with each species almost to below detection threshold levels. The amount of each species in the product relative to feedstock was reduced in: glyceric acid by about 87-90% (~88.5%); glycolic acid by about 86-88% (~87.2%); formic acid by about 97-99% (~99.2%); lactic acid by about 97-99% (~98.8%); and acetic acid by about almost 99-100% 100% (<0.2%), below detectable levels.

TABLE 6

|  | Sodium (Na) ppm | Glyceric Acid g/L | Glycolic Acid g/L | Formic Acid g/L | Lactic Acid g/L | Acetic Acid g/L |
|---|---|---|---|---|---|---|
| Feedstock | 1620. | 0.026 | 0.055 | 0.243 | 4.123 | 0.391 |
| Product | 33.6 | 0.003 | 0.007 | 0.002 | 0.051 | 0.000 |
| % reduct. | 97.9 | 88.5 | 87.3 | 99.2 | 98.7 | 99.9 |

Without the presence of organic acids and salts in the distillation bottoms, one can minimize if not eliminate side-reactions that form epoxides, like propylene oxide and glycidol, esters and other odor or color contributing species, which are unacceptable in commercial USP grade products. Table 7, presents the results of an analysis of distillation bottom products. Without salts in the distillation bottoms, the incidence of side reactions that form propylene oxide (PO), glycidol, colorants or odorants are diminished significantly.

TABLE 7

| Treatment | Propylene Oxide/ Glycidol (ppm) | Lactic acid (%) | Color | Di-PG (%) |
|---|---|---|---|---|
| Ion Exclusion | 0.0 | 0.51 | Light Yellow | 0.74 |
| Neutralization | 0.46 | 9.4 | Brown | 1.67 |

Table 8, presents the results of an analysis of distillate contents. The amount of undesired contaminants and side-products in the distillate fraction are decreased when one changes the treatment from the conventional acid neutralization to the present ion-exclusion. One can halve the amount of BDO and remove odor producing compounds without significant effect on the percentage yield of propylene glycol.

TABLE 8

| Treatment | BDO (%) | Proplene Glycol (%) | Odor | Ethylene Glycol (%) |
|---|---|---|---|---|
| Ion Exclusion | 0.60 | 94.41 | None | 4.42 |
| Neutralization | 1.57 | 94.50 | Strong | 3.97 |

Table 9, summarizes the compositions of process streams have been subject to the present inventive process, which have largely removed or eliminated the extraneous organic acids or salts according to the present invention. The streams are analyzed for the content of each species present. The fractions given for each species is expressed in terms of percent relative area of a gas chromatograph (% RA). As one can discern from the foregoing tables, significant reduction in the contaminant species is achieved.

TABLE 9

| Example | Description | Propylene Oxide (derivitized) LC method) (ppm) | Glycidol (derivitized) LC method) (ppm) | KF moisture (%) | % Relative Area of Gas Chromatograph ||||||| 
|---|---|---|---|---|---|---|---|---|---|---|---|
|  |  |  |  |  | Methanol | Ethanol | Propylene Oxide | Acetone | 2-Propanol | Allyl Alcohol | 1-Propanol |
| 1 | Dewatering Feed (ARC Bottoms) | ND | ND | 66.5 | 0.0003 | 0 | 0.000477 | 0.000 | 0 | 0 | 0.000 |
| 2 | Dewatering Bottoms (GRC feed) | ND | ND | 0.9 | 0.0000 | 0 | 0 | 0.000 | 0 | 0 | 0.000 |
| 3 | GRC bottoms | ND | ND | 2.6 | 0.0000 | 0 | 0 | 0.000 | 0 | 0 | 0.000 |
| 4 | WRC distillate | 0.66 | ND | 100.3 | 6.4 | 1.5 | 0 | 1.2 | 0.142 | 0 | 0.809 |
| 5 | EGC bottoms | ND | ND | 2.0 | 0.0000 | 0 | 0 | 0.000 | 0 | 0 | 0.000 |
| 6 | EGC distillate | 2.4 | 149 | 2.4 | 0.0004 | 0 | 0.000471 | 0.001 | 0 | 0 | 0.000 |
| 7 | PGC bottoms | ND | ND | 0.14 | 0.0000 | 0 | 0 | 0.000 | 0 | 0 | 0.000 |
| 8 | PGC distillate | 2.5 | 334 | 49.4 | 0.0122 | 0.0013 | 0.000362 | 0.033 | 0 | 0 | 0.005 |

TABLE 9-continued

| Example | Description | | | | | | | | | |
|---|---|---|---|---|---|---|---|---|---|---|
| 9 | GRC distillate | 2.5 | 506 | 1.7 | 0.0001 | 0 | 0.000502 | 0.000 | 0 | 0 | 0.000 |

| | | % Relative Area of Gas Chromatograph | | | | | | | | | |
|---|---|---|---|---|---|---|---|---|---|---|---|
| Example | Description | 2-Butanol | Iso-Butyl Alcohol | Hydroxy-acetone | 3-Hydroxy-2-Butanone | Glycidol | Ethylene Glycol | Propylene Glycol | 2,3-Butane diol 1 | 2,3-Butane diol 2 | 3-Methyl Cyclo-pentanol |
| 1 | Dewatering Feed (ARC Bottoms) | 0.00 | 0.00 | 0.003 | 0.004 | 0.0002 | 3.0 | 84.1 | 0.288 | 0.300 | 0 |
| 2 | Dewatering Bottoms (GRC feed) | 0.00 | 0.00 | 0.000 | 0.000 | 0.0006 | 3.1 | 83.7 | 0.295 | 0.305 | 0 |
| 3 | GRC bottoms | 0.00 | 0.00 | 0.000 | 0.000 | 0.0027 | 0.299 | 2.4 | 0.002 | 0.003 | 0 |
| 4 | WRC distillate | 0.00 | 0.00 | 0.258 | 1.822 | 0.0000 | 1.3 | 54.4 | 1.3 | 1.4 | 5.82 |
| 5 | EGC bottoms | 0.00 | 0.00 | 0.000 | 0.001 | 0.0000 | 38.2 | 54.7 | 0.001 | 0.009 | 0 |
| 6 | EGC distillate | 0.00 | 0.00 | 0.007 | 0.000 | 0.0153 | 0.59 | 98.4 | 0.329 | 0.332 | 0.0003 |
| 7 | PGC bottoms | 0.00 | 0.00 | 0.000 | 0.000 | 0.0000 | 0.62 | 99.2 | 0.000 | 0.010 | 0.0001 |
| 8 | PGC distillate | 0.00 | 0.00 | 0.261 | 0.009 | 0.0444 | 0.013 | 73.2 | 11.8 | 9.2 | 0.0055 |
| 9 | GRC distillate | 0.00 | 0.00 | 0.003 | 0.000 | 0.0441 | 3.5 | 95.1 | 0.303 | 0.306 | 0.0004 |

| | | % Relative Area of Gas Chromatograph | | | | | | | | | |
|---|---|---|---|---|---|---|---|---|---|---|---|
| Example | Description | 1,2-Butane diol 1 | 2,3-Pentane diol 1 | 1,3-Butane diol | 2,3-Pentene diol 2 | 1,4-Butane diol 1 | Diethylene Glycol | 2,5 Hexane diol | Glycerol | Dipropylene Glycol 1 | Dipropylene Glycol 2 |
| 1 | Dewatering Feed (ARC Bottoms) | 0.089 | 0.058 | 0.009 | 0.069 | 0.001 | 0.002 | 0.143 | 11.4 | 0.000 | 0.10 |
| 2 | Dewatering Bottoms (GRC feed) | 0.095 | 0.054 | 0.006 | 0.068 | 0.001 | 0.002 | 0.146 | 11.6 | 0.001 | 0.15 |
| 3 | GRC bottoms | 0.003 | 0.000 | 0.000 | 0.001 | 0.004 | 0.001 | 0.362 | 92.0 | 0.000 | 0.25 |
| 4 | WRC distillate | 0.047 | 0.352 | 0.000 | 0.096 | 0.000 | 0.000 | 0.000 | 4.9 | 0.000 | 0.21 |
| 5 | EGC bottoms | 0.976 | 0.002 | 0.001 | 0.024 | 0.001 | 0.032 | 1.301 | 0.038 | 0.000 | 2.27 |
| 6 | EGC distillate | 0.026 | 0.071 | 0.006 | 0.070 | 0.001 | 0.000 | 0.001 | 0.001 | 0.060 | 0.002 |
| 7 | PGC bottoms | 0.024 | 0.004 | 0.005 | 0.067 | 0.001 | 0.001 | 0.000 | 0.001 | 0.001 | 0.002 |
| 8 | PGC distillate | 0.066 | 2.067 | 0.029 | 0.040 | 0.002 | 0.002 | 0.005 | 0.008 | 1.889 | 0.008 |
| 9 | GRC distillate | 0.098 | 0.067 | 0.006 | 0.063 | 0.001 | 0.001 | 0.078 | 0.012 | 0.055 | 0.151 |

D. Utilization of Ion Exclusion Chromatography with Ion Exchange

According to the present, invention, ion exclusion chromatography either alone or in combination with ion exchange is a cost effective way to reduce the salt load in a liquid sample from >7.5% to <5 ppm. The following examples demonstrate that employment of IEC and ion-exchange techniques can significantly reduce salt loads and harness the advantages of both techniques. Example 1 shows the relative efficiency of using ion exchange alone. Example 2 shows the efficiency of IEC, and Example 3 shows a comparative resin load for each technique.

Example 1

Ion Exchange (IX)

Using a PG-reactor product feed stream that has 75,386 ppm of predominantly sodium sulfate salt, a desired product should have <5 ppm sodium sulfate. This salt was removed using ion exchange only and treated as follows:

75,386 ppm sodium sulfate=24,404 ppm sodium+50,982 ppm sulfate=1.0615 Eq/L sodium and 0.5308 Eq/L sulfate. A SAC resin is used with a stated capacity of 1.8 Eq/L and WBA with the same 1.8 Eq/L. This resin in this application was able to treat as follows:

Resin volume=Total Eq (in liter of feed)/Resin Capacity (Eq/L)*safety factor

Bed Volume (BV) capacity=equivalent volumes treated=Feed quantity/Total resin volume required per liter of feed SAC resin: Resin volume=1.0615 Eq/L/1.8 Eq/L*1.1
Resin volume=0.649 L required to treat 1 liter of feed
Bed volume Capacity=1 L/0.649=1.5416 equivalent volumes treated/cycle
WBA resin: Resin volume=0.5308 Eq/L/1.8 Eq/L*1.1
Resin volume=0.324 L required to treat 1 liter of feed
Bed volume Capacity=1 L/0.324=3.0831 equivalent volumes treated/cycle Example 2

Ion Exclusion Chromatography (IEC)

In contrast to Example 1, above, a similar product feed stream containing from 200-2000 ppm sodium as sodium sulfate was subjected to IEC treatment. One started with 2000 ppm sodium as sodium sulfate=2000 ppm sodium with 4178 ppm sulfate, and the process ran as follows:
SAC resin: Resin volume=0.087 Eq/L/1.8 Eq/L*1.1
Resin volume=0.053 L required to treat 1 liter of feed
Bed volume Capacity=1 L/0.053=18.81 equivalent volumes treated/cycle
WBA resin: Resin volume=0.0435 Eq/L/1.8 Eq/L*1.1
Resin volume=0.027 L required to treat 1 liter of feed
Bed volume Capacity=1 L/0.027=37.6 equivalent volumes treated/cycle When one used 200 ppm sodium as sodium sulfate=200 ppm sodium with 417.8 ppm sulfate, one produced:
SAC resin: Resin volume=0.0087 Eq/L/1.8 Eq/L*1.1
Resin volume=0.0053 L required to treat 1 liter of feed
Bed volume Capacity=1 L/0.0053=188.1 equivalent volumes treated/cycle
WBA resin: Resin volume=0.00435 Eq/L/1.8 Eq/L*1.1
Resin volume=0.0027 L required to treat 1 liter of feed
Bed volume Capacity=1 L/0.0027=376.2 equivalent volumes treated/cycle.

Example 3

IEC and Ion Exchange Comparative Resin Load

In this example a flow of 200 Liters/minute (LPM) was used with regeneration every 8 hours. Starting without IEC treatment ionic load=75,386 ppm sodium sulfate=24,404 ppm sodium+50,982 ppm sulfate=1.0615 Eq/L sodium and 0.5308 Eq/L sulfate. A SAC resin was used with a stated capacity of 1.8 Eq/L and WBA with the same 1.8 Eq/L. The results are as follows:
SAC resin: Resin volume/min=200*1.0615 Eq/L/1.8 Eq/L*1.1
Resin volume/min=129.74 L/min required to treat feed
Resin volume/8 hours=129.74*8*60=62,275 L of resin
WBA resin: Resin volume/min=200*0.5308 Eq/L/1.8 Eq/L*1.1
Resin volume/min=64.87 L/min required to treat feed
Resin volume/8 hours=64.87*8*60=31,138 L of resin Using IEC product with 200 ppm sodium the results are:
SAC resin: Resin volume/min=200*0.0087 Eq/L/1.8 Eq/L*1.1
Resin volume/min=1.063 L/min required to treat feed
Resin volume/8 hours=1.063*8*60=510.4 L of resin
WBA resin: Resin volume/min=200*0.0043 Eq/L/1.8 Eq/L*1.1
Resin volume/min=0.532 L/min required to treat feed
Resin volume/8 hours=0.532*8*60=255.2 L of resin When the salt content in the product of IEC treatment was as low as 50 ppm, the ion exchange system was able to process four times the volumes used at 200 ppm. Regeneration chemical usage for each of the preceding scenarios was the same, but after undergoing IEC pretreatment the ion exchange system was able to process much more feed material than when used without prior IEC treatment.

Benefits of this effect permits one to prolong the useful life of the ion exchange resins, either by using the same column size as without IEC (Example 1), but regenerated much less frequently, or by decreased resin column size when using IEC (Example 2), regenerated as frequently as the larger system as without IEC (Example 3).

The present invention has been described in general and in detail by way of examples. Persons of skill in the an understand that the invention is not limited necessarily to the embodiments specifically disclosed, but that modifications and variations may be made without departing from the scope of the invention as defined by the following claims or their equivalents, including other equivalent components presently known, or to be developed, which may be used within the scope of the present invention. Therefore, unless changes otherwise depart from the scope of the invention, the changes should be construed as being included herein.

We claim:

1. A method for reducing contaminants in the production of a glycol product of hydrogenolysis, the method comprises: providing a renewable or bio-derived feedstock; reacting said feedstock in a reactor to produce an aqueous, polyol product mixture; subjecting said product mixture to ion-exclusion chromatography without pH adjustment to separate and reduce salts of organic acids, from an eluant fraction containing a desired product; and distilling said eluant fraction to yield a glycol.

2. The method according to claim 1, further comprises: subjecting said product mixture without pH neutralization to ion-exchange in addition to ion-exclusion chromatography.

3. The method according to claim 1, wherein said polyol product mixture is generated from a reaction between renewably-sourced carbohydrates with hydrogen, and contains organic acids, salts, diols, and unreacted feedstock.

4. The method according to claim 1, wherein said product mixture has an alkaline pH value between about 8.0 and about 12.0 when extracted initially from said reactor.

5. The method according to claim 1, wherein said product mixture is not first neutralized with an acid.

6. The method according to claim 1, wherein said product mixture is introduced into a continuous ion-exclusion chromatography system.

7. The method according to claim 6, wherein said continuous system is a simulated-moving bed chromatography system.

8. The method according to claim 1, wherein said ion-exclusion chromatography uses a resin selected from a gel-type strong acid cation (SAC) resin, gel-type strong base anion (SBA) resin, or macroporous resin.

9. The method according to claim 1, wherein an amount of about 0.01-80 g/kg of BDO or PDO is removed per kilogram of propylene glycol recovered.

10. The method according to claim 1, wherein said eluent fraction is introduced directly from said chromatography system to a distillation column.

11. The method according to claim 1, wherein said distilling comprises a first column that removes alcohols, a second column that removes water, a third column that removes unreacted components or organic components having higher boiling points than that of ethylene glycol, a fourth column that removes ethylene glycol, and a fifth column that removes epoxides, esters, $C_4$ and higher diols, residual water, and propylene glycol.

12. A method of manufacturing propylene glycol or ethylene glycol, the method comprises providing a biologically-derived feedstock of three, five, and six carbon sugars or sugar alcohols;

converting by hydrogenolysis said feedstock in a reactor to a reaction product mixture containing polyols and impurities; subjecting said reaction product mixture to ion-exclusion chromatography to reduce said impurities from an eluant fraction containing propylene glycol or ethylene glycol; distilling said eluant fraction through a distillation system having a first column that removes alcohols, a second column that removes water, a third column that removes unreacted components or organic components having higher boiling points than that of ethylene glycol, a fourth column that removes ethylene glycol, and a fifth column that removes epoxides, esters, $C_4$ $C_5$ and higher diols, residual water and propylene glycol.

13. The method according to claim 12, wherein said reaction product mixture is introduced without first neutralizing with acid into said ion-exclusion chromatography.

14. The method according to claim 12, wherein said ion-exclusion chromatography is part of a continuous, simulated-moving bed system.

15. The method according to claim 12, wherein said impurities include organic acids, salts, diols, and unreacted feedstock.

16. The method according to claim 12, wherein bottoms content from said third distillation column is recyclable directly into said reactor.

17. The method according to claim 12, wherein said reaction product mixture has an alkaline pH value that is not neutralized after retrieval from said reactor.

18. The method according to claim 12, further includes extracting and introducing said elution fraction directly into said distillation system.

19. The method according to claim 12, wherein said method about 87% to about 99% of organic acids and salts from an initial feedstock relative to said organic acids and salts in a product.

20. The method according to claim 12, further comprises: subjecting said reaction product mixture to ion-exchange.

* * * * *